US009452034B1

(12) United States Patent
Urquiola

(10) Patent No.: US 9,452,034 B1
(45) Date of Patent: Sep. 27, 2016

(54) HYBRID PASSIVELY FITTING PROSTHODONTIC FRAMEWORKS

(71) Applicant: Javier Urquiola, Fort Lee, NJ (US)

(72) Inventor: Javier Urquiola, Fort Lee, NJ (US)

(*) Notice: Subject to any disclaimer, the term of this patent is extended or adjusted under 35 U.S.C. 154(b) by 162 days.

(21) Appl. No.: 14/060,244

(22) Filed: Oct. 22, 2013

Related U.S. Application Data

(60) Provisional application No. 61/717,483, filed on Oct. 23, 2012.

(51) Int. Cl.
| A61C 13/01 | (2006.01) |
| A61C 13/34 | (2006.01) |
| A61C 13/15 | (2006.01) |
| A61C 8/00 | (2006.01) |
| A61K 6/04 | (2006.01) |

(52) U.S. Cl.
CPC .......... *A61C 13/01* (2013.01); *A61C 8/005* (2013.01); *A61C 13/34* (2013.01); *A61C 19/003* (2013.01); *A61K 6/04* (2013.01)

(58) Field of Classification Search
CPC .... A61C 8/0048; A61C 13/01; A61C 13/34; A61C 19/003; A61C 8/005; A61K 6/04
USPC .......................................... 433/172–176, 180
See application file for complete search history.

(56) References Cited

U.S. PATENT DOCUMENTS

| 1,183,396 A * | 5/1916 | Morgan ........................ 433/183 |
| 4,062,119 A * | 12/1977 | Linkow et al. ............... 433/176 |
| 4,767,328 A * | 8/1988 | Branemark .................. 433/168.1 |
| 4,986,753 A * | 1/1991 | Sellers ........................... 433/172 |
| 5,219,286 A * | 6/1993 | Hader ............................ 433/172 |
| 5,234,339 A * | 8/1993 | Grigereit ....................... 433/172 |
| 5,427,906 A | 6/1995 | Hansen |
| 5,630,717 A * | 5/1997 | Zuest et al. ................... 433/172 |
| 5,885,078 A | 3/1999 | Cagna et al. |
| 6,056,547 A | 5/2000 | Names |
| 6,322,364 B1 * | 11/2001 | Oshida et al. ................ 433/173 |
| 6,905,336 B2 * | 6/2005 | Summers ...................... 433/214 |
| 7,207,799 B2 * | 4/2007 | Fisher et al. .................. 433/172 |
| 7,214,061 B2 * | 5/2007 | Fortin ............................ 433/173 |
| 7,699,611 B2 * | 4/2010 | Feijtel ........................... 433/173 |
| 7,985,071 B2 | 7/2011 | Weissman |
| 8,100,692 B2 * | 1/2012 | Diangelo et al. ............. 433/213 |
| 8,137,103 B1 | 3/2012 | Freilich et al. |
| 2003/0108845 A1 | 6/2003 | Giovannone et al. |
| 2004/0018469 A1* | 1/2004 | Summers ...................... 433/173 |
| 2004/0166476 A1 | 8/2004 | Weissman |
| 2005/0019727 A1 | 1/2005 | McGlumphy et al. |
| 2005/0019728 A1 | 1/2005 | Rostagno et al. |
| 2009/0081618 A1 | 3/2009 | LaMar |
| 2010/0297574 A1* | 11/2010 | Llop et al. ....................... 433/75 |

(Continued)

OTHER PUBLICATIONS

Aparicio, *A New Method to Routinely Achieve Passive Fit of Ceramometal Prostheses Over Branemark Osseointegrated Implants: A Two-Year Report*, Int J Periodontics Restorative Dent., Oct. 1994, 14(5):404-419.

(Continued)

*Primary Examiner* — Cris L Rodriguez
*Assistant Examiner* — Hao D Mai

(57) ABSTRACT

The invention provides improved passively fitting, permanent, detachable frameworks for supporting dental restorations on osseo-integrated dental implants, methods for making the frameworks and methods of using the frameworks.

15 Claims, 13 Drawing Sheets

(56) References Cited

U.S. PATENT DOCUMENTS

2012/0064489 A1    3/2012   Rubbert et al.
2012/0088208 A1    4/2012   Schulter et al.
2012/0109140 A1*   5/2012   Akutsu ........................ 606/96

OTHER PUBLICATIONS

Briccoli et al., *A technique for fabricating a definitive immediate implant-supported prosthesis for the edentulous mandible*, J Prosthet Dent, 2012, 108:196-199.

Hatjigiorgis et al., A Novel Framework to Eliminate the Effects of Casting Distortion when Fabricating a Fixed, Detachable Screw-Retained Prosthesis, *Journal of Prosthodontics*, Journal of Prosthodontics, 2012, 21:478-481.

Swallow, *Technique for Achieving a Passive Framework Fit: A Clinical Case Report*, Journal of Oral Implantology, 2004, vol. XXX, No. 2: 83-92.

Clinical Innovations Presentations Announcement listing presentation of J. Urquiola No. CI-6 "Achieving a More Passively Fitting Metal-Resin Fixed-Detachable Prosthesis by Utilizing a Framework that Allows for Creep." for the Academy of Osseointegration's 31st Annual Meeting, Feb. 17-20, 2016 in San Diego, CA.

Urquiola, J., Abstract "Achieving a More Passively Fitting Metal-Resin Fixed-Detachable Prosthesis by Utilizing a Framework that Allows for Creep" submitted to and accepted for presentation at the Academy of Osseointegration's 31st Annual Meeting, Feb. 17-20, 2016 in San Diego, CA.

\* cited by examiner

HYBRID PASSIVELY FITTING PROSTHODONTIC FRAMEWORKS

CROSS-REFERENCE TO RELATED APPLICATIONS

This application claims the benefit of U.S. provisional application Ser. No. 61/717,483 filed Oct. 23, 2012, which is hereby incorporated by reference in its entirety.

FIELD OF THE INVENTION

The invention relates to the field of prosthodontics.

BACKGROUND OF THE INVENTION

A fixed, detachable prosthesis is a multiple implant prosthesis that requires a precisely fitting screw-retained framework. An ill-fitting framework typically must be sectioned and soldered or welded to achieve an acceptable fit. Maladies such as bone loss around the implants, screw loosening, screw breakage, and implant and prosthesis fracture have all been attributed to ill-fitting frameworks. When fabricating a screw-retained fixed, detachable restoration one goal is to mitigate the sources of distortion so when the final sum of distortion is paired with chewing, the resultant stress on the implant-prosthesis complex is less than the biologic tolerance, therefore leading to an acceptable outcome with no complications. Since a particular patient's biologic tolerance cannot be-predicted, the goal is to introduce no distortion or as little as possible throughout the process of manufacturing the prosthesis. An ideal fixed, detachable framework sits passively on the implants and does not introduce any stress. While several techniques have been proposed for the fabrication of passively fitting frameworks, these techniques require extra visits, chairtime, and laboratory time and only mitigate rather than eliminate the stresses due to imperfectly matched frameworks and implants.

What is needed and provided by the present invention are new and improved types of passively fitting prosthodontic frameworks and methods for fabricating the frameworks.

SUMMARY OF THE INVENTION

One embodiment of the invention provides a one-piece, elongated passively fitting framework component having a tissue side and an occlusal side that includes:

a first lateral surface-presenting, abutment-facing segment;

a second lateral surface-presenting, abutment-facing segment; and a connecting segment, such as an elongated connecting segment, joining the first lateral surface-presenting, abutment-facing segment and the second lateral surface-presenting, abutment-facing segment, or the first and second lateral surface-presenting, abutment-facing segments directly joined to each other.

A related embodiment of the invention provides a one-piece, elongated passively fitting framework component having a tissue side and an occlusal side that includes:

a plurality of sequentially ordered lateral surface-presenting, abutment-facing segments; and for each adjacent pair of sequentially ordered lateral surface-presenting, abutment-facing segments, a connecting segment, such as an elongated connecting segment joining the pair or the pair being directly joined to each other.

Another embodiment of the invention provides a one-piece, solid, elongated passively fitting framework component having a tissue side and an occlusal side, that includes:

a terminal screw attachment portion forming a hole passing from the tissue side to the occlusal side of the component;

lateral surface-presenting, abutment-facing segment; and a connecting segment, such as an elongated connecting segment, joining the terminal screw attachment portion and the lateral surface-presenting, abutment-facing segment or the terminal screw attachment portion and the lateral surface-presenting, abutment-facing segment directly joined to each other. The component may optionally include further lateral surface-presenting, abutment-facing segments which may be connected by interposed connecting segments.

A further embodiment of the invention provides a one-piece, solid elongated passively fitting framework component having a tissue side and an occlusal side, that includes:

a terminal screw attachment portion forming a hole passing from the tissue side to the occlusal side of the component;

a first lateral surface-presenting, abutment-facing segment;

a first connecting segment, such as a first elongated connecting segment, joining the terminal screw attachment portion and the first lateral surface-presenting, abutment-facing segment;

a second lateral surface-presenting, abutment-facing segment; and a second connecting segment, such as a second elongated connecting segment, joining the first lateral surface-presenting, abutment-facing segment and the second lateral surface-presenting, abutment-facing segment.

Still another embodiment of the invention provides a one-piece elongated passively fitting framework component having a tissue side and an occlusal side that includes or consists essentially of:

a first portion selected from the group consisting of a terminal screw attachment portion forming a hole passing from the tissue side to the occlusal side of the component and a terminal C-shaped abutment-surrounding segment defining a concavity;

a second portion including a lateral surface-presenting, abutment-facing segment; and a connecting segment, such as an elongated connecting segment, joining the first portion to the second portion or the first and second portions being directly joined.

The invention also provides hybrid passively fitting frameworks that include:

an elongated passively fitting framework component according to any one of embodiments or variations thereof described herein;

an abutment sleeve, such as a primary abutment sleeve or a secondary abutment sleeve, facing the lateral surface of the lateral surface-presenting, abutment-facing segment, for example disposed at least partially in the concavity of a C-shaped lateral surface-presenting, abutment-facing segment; and a hardened resin joining each abutment sleeve to the lateral surface-presenting, abutment-facing segment it faces. At least some, such as at least one or all, of the abutment sleeves may be externally ribbed. Non-ribbed abutment sleeves may also be used. The abutment sleeves may be metallic such as titanium or titanium alloy.

A lateral surface-presenting, abutment-facing segment may, for example, be a lateral concavity-presenting abutment-surrounding segment such as but not limited to a C-shaped or V-shaped abutment-surrounding segment.

The invention further provides dental restorations for detachable, fixed attachment to osseo-integrated dental implants that include: a hybrid passively fitting framework and any variations thereof as described herein; and a tooth set-up attached to the hybrid passively fitting framework.

The invention also provides methods for fabricating the elongated framework components described herein and the hybrid passively fitting frameworks that include such a component.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

DETAILED DESCRIPTION OF THE INVENTION

The invention provides new types of passively fitting prosthodontic frameworks and rapid methods for fabricating the frameworks and components thereof.

Figure 1:
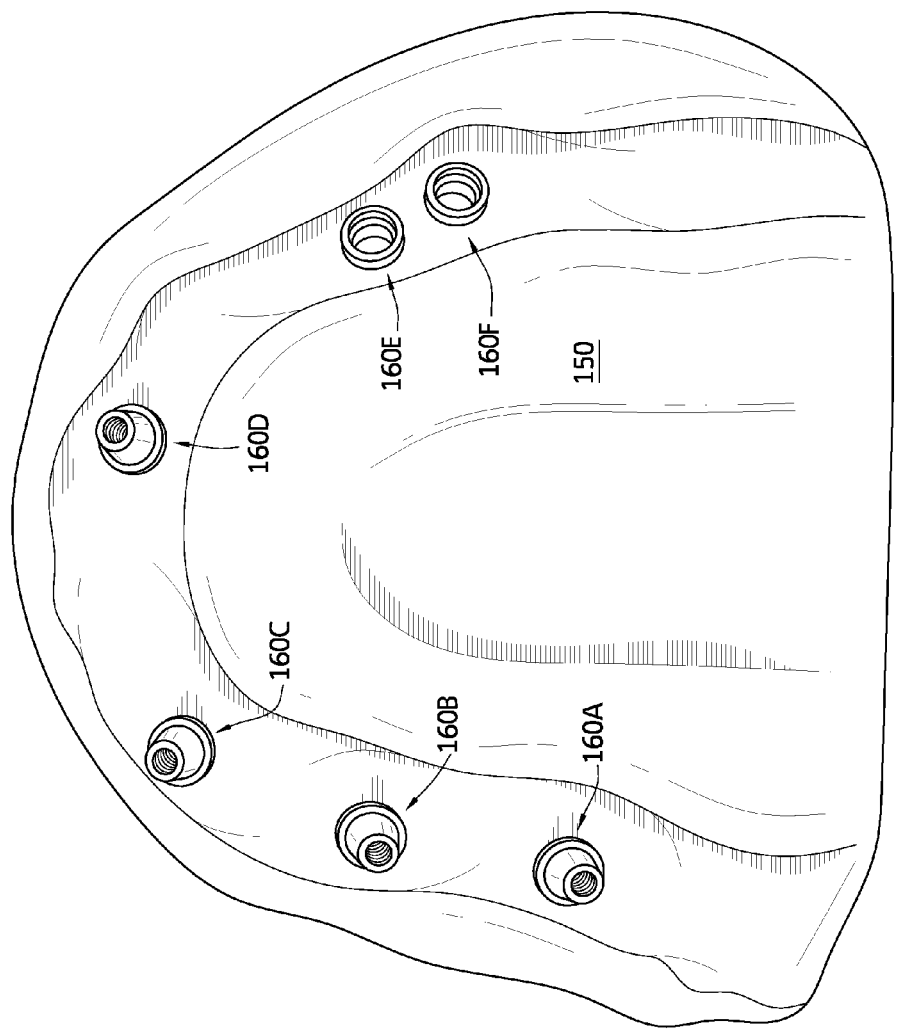
FIG. 1 shows a stone cast model of a patient's mouth having six osseo-integrated dental implants.

FIG. 1 shows a stone cast model of a patient's mouth 150 that include six osseo-integrated oral implants at positions 160A-F. Primary abutments are shown screwed into the dental implants at positions 160A-160D. The primary abutments are internally threaded so that a secondary abutment may be reversibly fixed thereto using a screw. As discussed further below, the primary abutments will later support secondary abutment sleeves of a passively fitting framework embodiment of the invention. In this embodiment, at positions 160E and F, abutment sleeves configured to directly mount to the dental implants via screw connection (not shown installed in FIG. 1), rather than to an intermediate primary abutment, were used.

Figure 2:
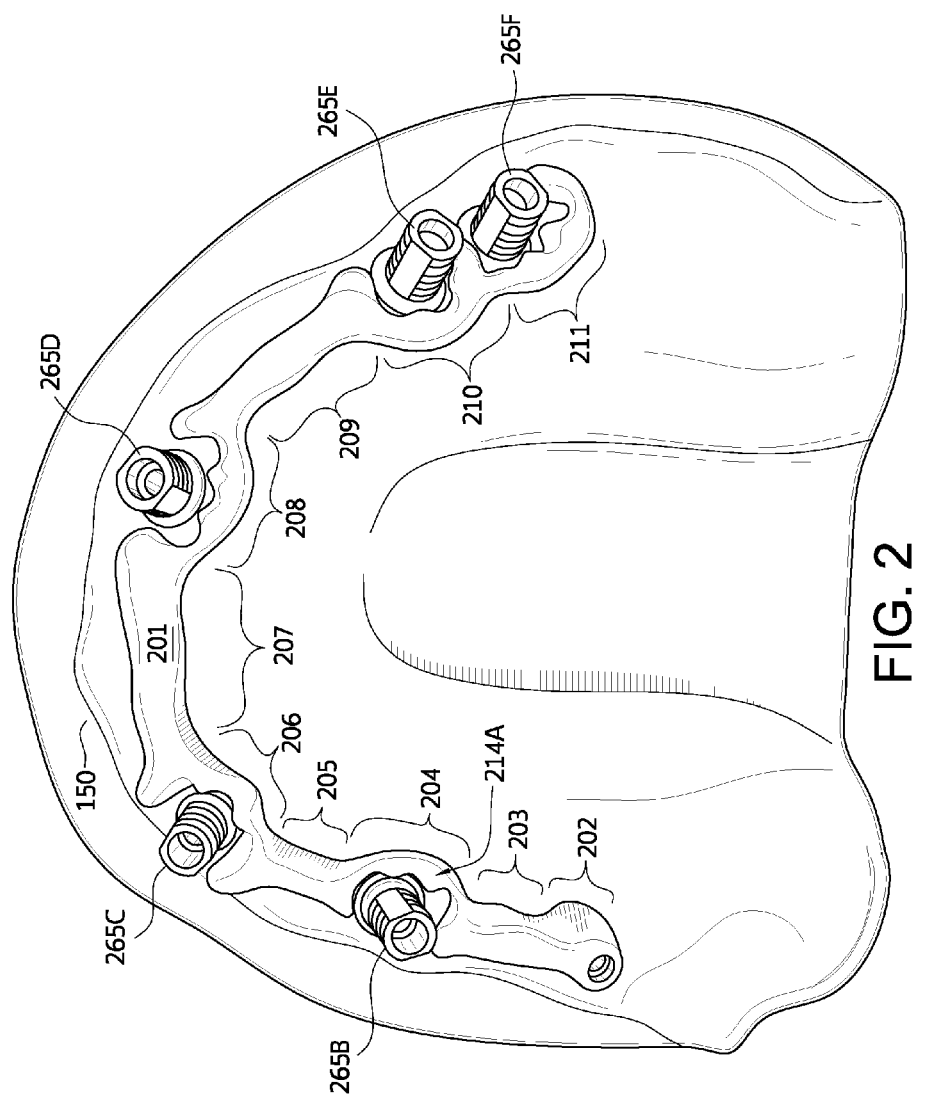
FIG. 2 shows an embodiment of a metallic framework component according to the invention that is fixed in the stone cast model of FIG. 1.

FIG. 2 shows a top view of the unitary metallic framework component 201 of a full arch embodiment of the invention positioned on hard model 150. The dental implants (not visible) are disposed into the patient's jawbone (and represented in the model) at positions 160A-F as shown in FIG. 1. At this point, a primary abutment (not visible) is screwed into each of the dental implants at positions 160A-D in the model. At each of positions 160B-D, a titanium sleeve secondary abutment, 265B-F respectively, is screw-connected to the primary abutment. At each of positions 160E and F, an abutment sleeve configured for direct attachment to a dental implant is reversibly fixed directly into the underlying dental implant using a screw. The abutment sleeves may, for example, be circumferentially ribbed as shown or have a non-ribbed outer surface. At one end of the elongated framework component is a screw attachment portion 202 in which a hole is formed for screw attachment of the prosthesis to a primary abutment which, in turn, is attached to the underlying dental implant. Proceeding from screw attachment portion 202 toward the opposite end of framework component 201 are connecting segments or "bars" 203, 205, 207, 209 that connect screw attachment portion 202 and abutment-surrounding segments 204, 206, 208, 210/211 to each other as shown. Specifically, screw attachment portion 202 is connected to abutment-surrounding segment 204 by connecting segment 203, abutment-surrounding segment 204 is connected to abutment-surrounding segment 206 by connecting segment 205, abutment-surrounding segment 206 is connected to abutment-surrounding segment 208 by connecting segment 207, abutment-surrounding segment 208 is connected to abutment-surrounding segment 210 by connecting segment 209. As shown, implant positions 160E and F are so close to each other that abutment connecting segments 210 and 211 are directly joined to one another by sharing a common segment there-between.

Viewed from the top (or bottom), each of the abutment connecting segments of framework component 201 is C-shaped (inclusive of U-shaped and crescent-shaped) having a convex side and a concave side. The shape of the abutment-surrounding segments generally defines a concavity (or recess) into which the titanium sleeve secondary abutment can be at least partially disposed (the central axes of the sleeves extending in a direction from the tissue side to the occlusal side). Framework component 201 has a generally arch-shaped profile following the gum line with a convex (facial/labial) side and a concave (lingual) side. As shown, the concave side of each abutment-surrounding segment opens on the convex side of framework component 201. Each of the abutment-surrounding segments has radial protrusions from its concave surface extending radially inward (e.g., 214A and 214B in abutment connecting segment 204). The ribs of the titanium abutment sleeves and the radial protrusions of the abutment-surrounding members facilitate the joining of the neighboring abutment sleeves and abutment-surrounding segments using polymer resin and help to transmit forces applied to the framework in the final dental restoration down into the attached dental implants. Although in framework component 201 all of the abutment-surrounding segments are commonly oriented with their openings being labial facing, the orientations of some or all of the abutment-surrounding segments could be such that their openings are lingual facing and/or labial facing and/or for abutment-surrounding segments at the end of a metallic framework component, labial-facing (facial), lingual-facing or opening in-line with the axis of the underlying jaw bone.

Screw attachment portion 202 is shown screwed to the underlying abutment at position 160A and framework 201 is thereby able to pivot on the screw connection when the screw connection is sufficiently loose. The connecting segments of framework component 201 have longitudinal axes (in the horizontal dimension shown) that generally follow the gum-line, i.e., the curvature of portion of the mandible or maxilla extensive with the restoration that is being prepared. Thus, the connecting segments and the abutment-surrounding segments are mutually sized and configured in framework component 201 so that the abutment-surrounding segments are able to partially surround and approach the titanium abutment sleeves whilst the connecting segments follow the curvature of portion of the mandible or maxilla extensive with the restoration that is being prepared.

Figure 3:
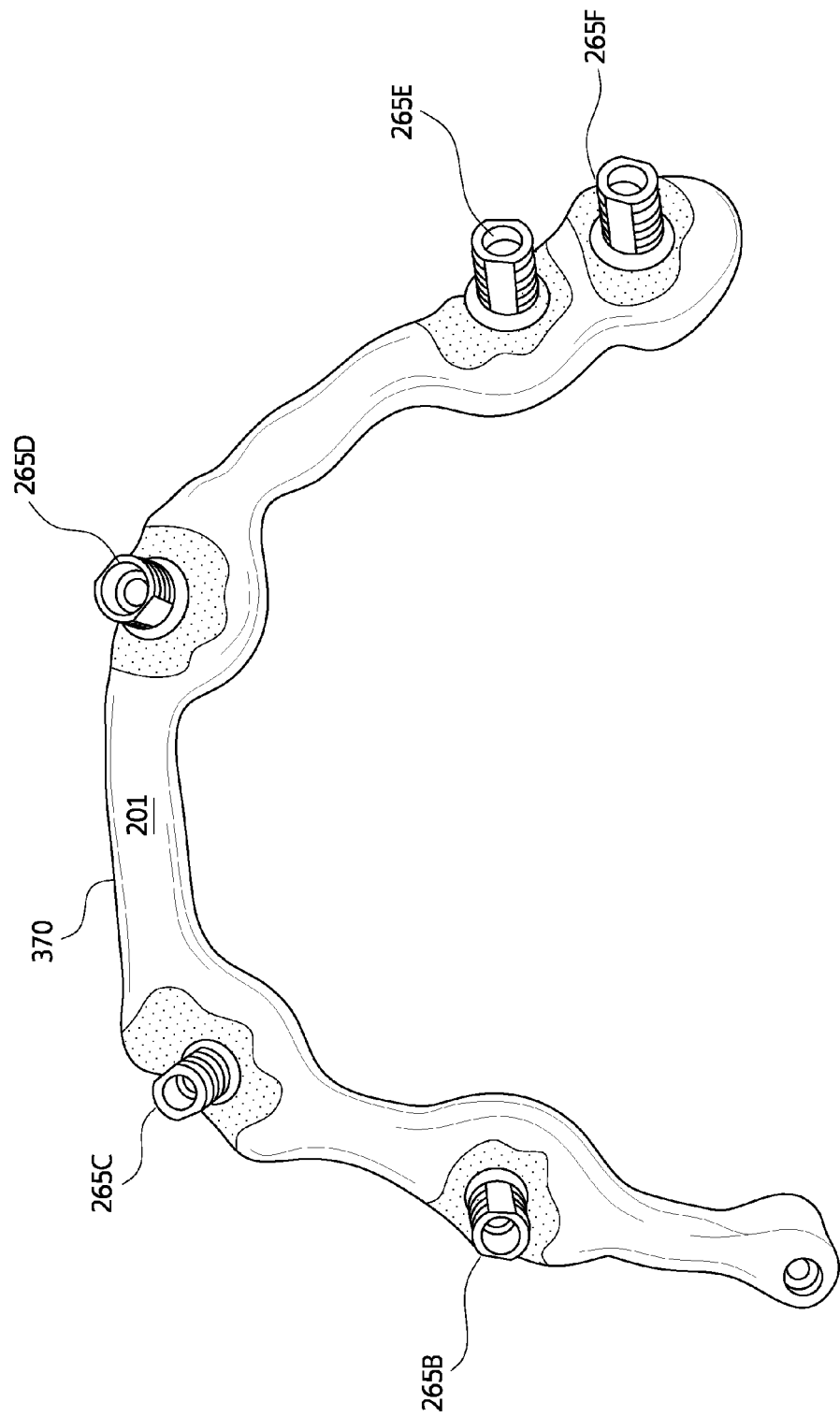
FIG. 3 shows a passively fitting, hybrid framework embodiment of the invention including the metallic framework component shown in FIG. 2.

A passively fitting framework is then formed in situ, in the patient's mouth. Abutment sleeves are reversibly attached (directly or indirectly via an intervening abutment as planned out using the model) to each of the dental implants in the patient's jaw bone using screws. Framework component 201 is attached to the dental implant corresponding to position 160A via screw connection portion 202 and set in a final position (by tightening the screw connection at portion 202) so that the abutment-surrounding segments of component 201 are facing the abutment sleeves (similarly to the view shown for the model in FIG. 2). Component 201 is then joined to each of secondary abutment sleeves 265B-F by filling in the space there-between with a hardening polymer resin such as an acrylic or a light-curable resin such as Triad® Gel (Dentsply International Inc., York, Pa., USA) or Primopattern LC Gel® (Primopattern, Bad Homburg, Germany). The resin bonds to the surfaces of the abutment-surrounding segments and the adjacent abutment sleeves and spans the space there-between. FIG. 3 shows the hybrid prosthodontic framework 370 so obtained, having been removed now from the patient's mouth. The hybrid framework includes the metallic framework component 201 joined by hardened resin to each of titanium sleeve abutments 265B-F. The use of a hardening/curable resin intra-orally as the joining material ensures that the resulting framework will be passively fitting. The invention also provides a related, but less preferable, method in which the hybrid framework is formed by joining the elongated component to the abutment sleeves using the resin while these members are attached to the oral model (such as shown in FIG. 2).

By the term "hybrid," what is meant herein is that the framework is formed of different materials joined together, namely an elongated one-piece framework component such as that described, one or more abutment sleeves and a hardened, curable polymer resin joining the elongated component and the abutment sleeve(s) to each other.

Optionally, once the resin has hardened, one or more of the abutment sleeves 265B-F can be welded to the metallic framework component 201 using metal spanning members such as rods.

Figure 4:
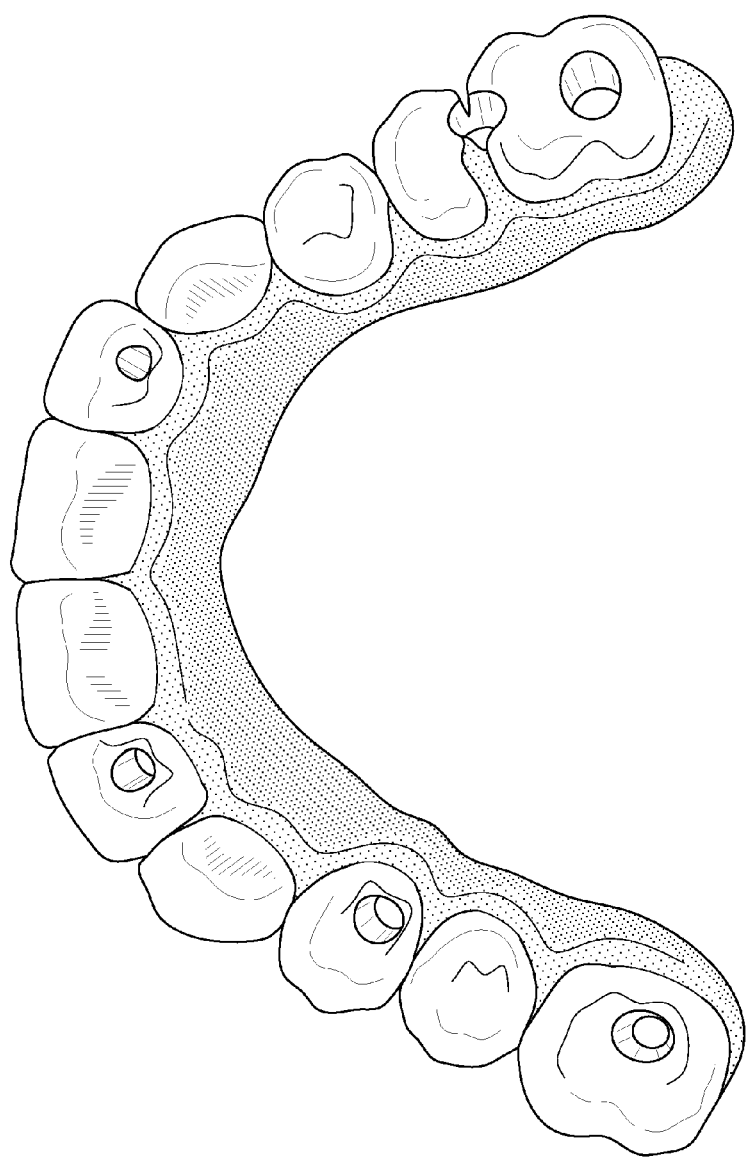
FIG. 4 shows the occlusal-side view of the completed permanent, detachable dental restoration that includes the hybrid framework embodiment of FIG. 3.
Figure 5:
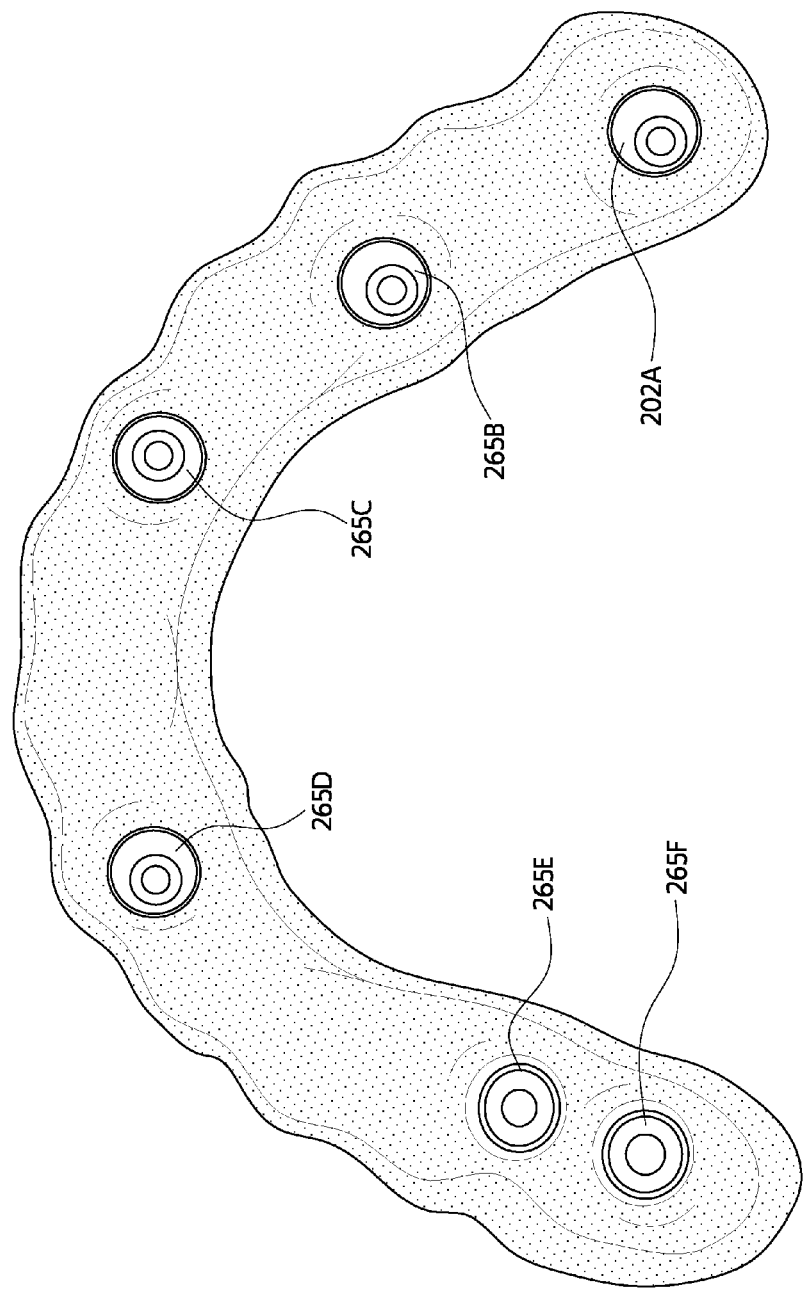
FIG. 5 shows the tissue-side view of the dental restoration shown in FIG. 4.

Hybrid framework 370 is then positioned over the dental implants in the patient's mouth and reversibly fixed by screw connection. Bite registration is recorded and an impression is made to create a new master model that preserves the new frame-implant position that was achieved. A tooth set-up may then be prepared on and around hybrid framework 370, for example, by any of the methods known in the art. FIG. 4 shows the occlusal side of the completed prosthesis. FIG. 5 shows the tissue side of the completed prosthesis with the interior surface of each abutment sleeve 265B-F as well as the primary abutment-interfacing surface of screw connection member 202A visible.

Figure 6:
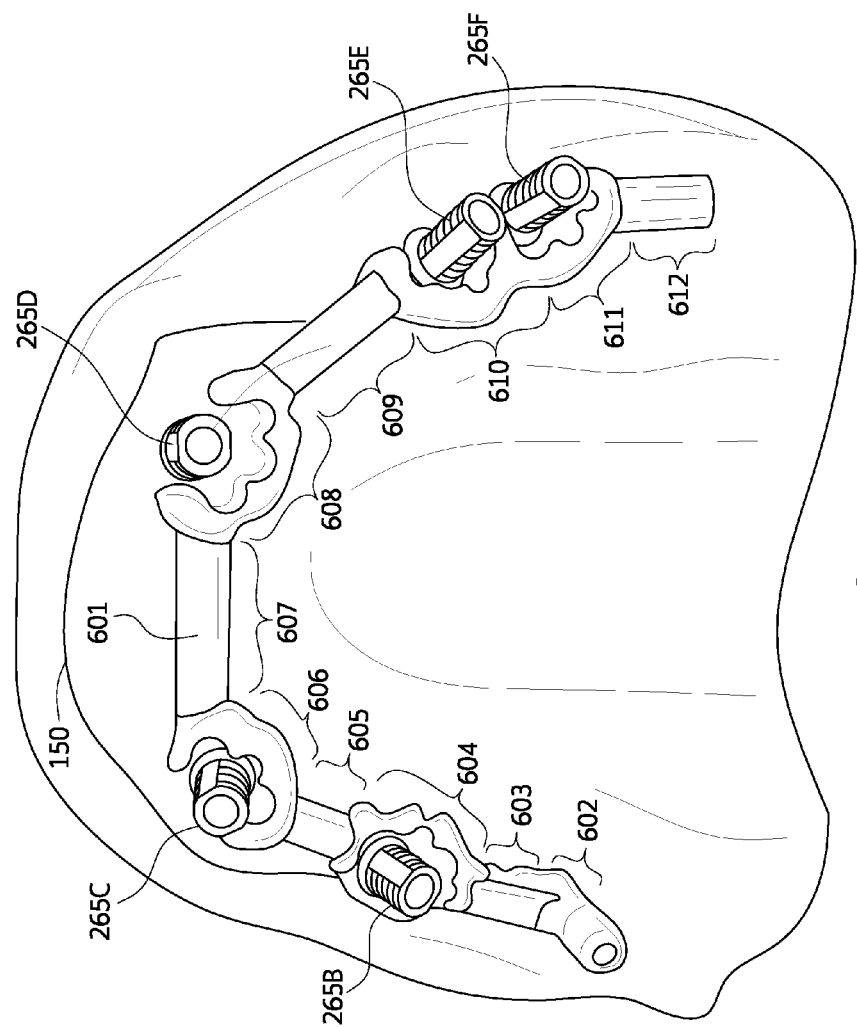
FIG. 6 shows the lost wax model used to cast the metallic framework component shown in FIG. 2.
Figure 7:
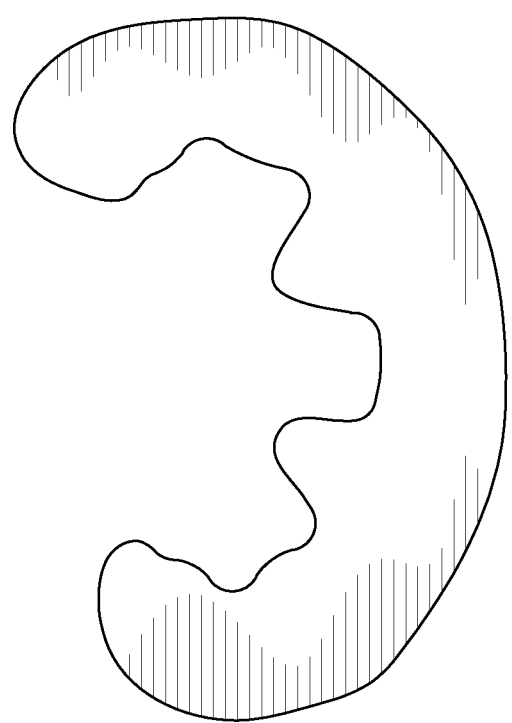
FIG. 7 shows an example of a castable model element for a C-shaped abutment-surrounding segment of an elongated framework component according to the invention.

Advantageously and in contrast to conventional frameworks, a metallic framework component according to the invention (such as component 201 of FIG. 2) may be formed from non-precious metals, for example, cobalt chromium alloys as known in the art such as Argeloy N.P. Special (The Argen Corporation, San Diego, Calif., USA). The metal content of Argeloy N.P. Special is 59.5% Co, 31.5% Cr, 5% Mo, 2% Si, and less than 1% each of Mn, Fe, and C. A framework component according to the invention, such as component 201, may be formed by any means. One preferred method involves forming a model of a metallic framework component of material, such as wax and/or acrylic, which can be burned out in a lost wax (investment) casting procedure. Since each metallic framework component is custom-made for a patient, a direct method of investment casting may be used. FIG. 6 shows stone cast model 150 of the patient's mouth with dental implants at positions 160A-F and titanium abutment sleeves 265B-F there-above. The burnable model 601 is composed of separate segments 602-611 that have been joined together by wax and/or acrylic resin and which correspond to sections 202-211 of the metallic framework component 201 of FIG. 2. Segment 612 is a sacrificial portion later removed from the resulting metallic casting. Connecting segments 603, 605, 607, 609 and segment 612 may be formed from castable modeling wax cut to length as needed. Screw attachment model portion 602 is formed of castable material and is sized and configured to precisely fit over the primary abutment screwed into the dental implant and provide surfaces for screw attachment of the corresponding cast portion to the primary abutment. Castable screw attachment members such as 602, which is essentially a castable model of a secondary abutment, are commercially available from implant and abutment manufactures or may be custom fabricated, for example from castable plastic or wax, as needed. Castable wax and/or acrylic, such as Pattern Resin™ (GC America, Inc., Alsip, Ill., USA), may be used to join separate elements of the castable model to one another, such as to join the screw attachment portion of the model to the adjacent connecting segment model portion and to build up surfaces around the screw attachment portion as needed or desired. Abutment-surrounding segments 604, 606, 608, 610 and 611 may for example each be individually formed from acrylic resin hardened in a silicone mold or alternatively formed of wax. FIG. 7 shows an individual castable C-shaped abutment-surrounding element of the kind that may be used to form a castable framework component model such as 601.

On the tissue side of the connecting segments (not visible in FIG. 6), additional thickness of material, such as castable molding wax, may be added to form tissue stop structures. When the castable model is completed, as shown in FIG. 6, it is removed from stone cast model 150 and used to cast the metallic framework component. Model 601 was used to cast metallic framework component 201 of FIG. 2. After casting, segment 612 was removed. The surface of the casting was ground to remove various sharp edges. The surface of the casting may be roughened by sand-blasting and/or by chemical etching. The roughening of the surface facilitates later bonding to acrylic or other resin used to join the metallic framework component to the abutment sleeves as well as bonding of the metallic framework components to the tooth set-up materials.

The abutment sleeves are types of abutments. It should be understood from this description that the abutment sleeves used may be secondary abutments that mount on primary abutments that in turn directly mount on underlying dental implants or the sleeves may be primary abutments themselves, i.e., mount directly to the underlying dental implants. As exemplified herein, a combination of these types of abutment sleeves may, if desired, be used in the manufacture of a hybrid framework of the invention or exclusively one type or the other may be used as desired. Similarly, although the example of the figures shows a terminal screw attachment portion of a framework component that is sized and configured to mount on a primary abutment, such portions that are sized and configured to directly mount on a dental implant may also be used. As used herein, when an abutment, such as an abutment sleeve, or a terminal screw attachment portion of a framework component is said to be fixed or connected or attached to a dental implant it may be either directly fixed or connected or attached to the implant or indirectly fixed or connected or attached to the implant via at least one, such as one, intermediate abutment. As well known in the art, abutment sleeves may be reversibly fixed to an underlying component, either another abutment or a dental implant, using a screw inserted into the shaft of the abutment sleeve and received by a threaded socket of the underlying component.

All of the various abutments described herein are commercially available for commonly used dental implants. Abutments are also commercially available in varying lengths and can also be readily truncated as needed. Abutments or a combination of abutments are selected so that the body of the abutment sleeve(s) that will be joined by resin to a C-shaped abutment-surrounding member of the elongate framework component extends into the plane of thickness of the C-shaped abutment-surrounding member when the elongate framework component is fixed in its operative position with respect to the patient's mouth or model thereof.

Without limitation, the invention also provides the following embodiments and variations thereof.

One embodiment of the invention provides a one-piece, solid, such as metallic, elongated passively fitting framework component having a tissue side and an occlusal side, that includes or consists essentially of or consists of:
 a terminal screw attachment portion forming a hole passing from the tissue side to the occlusal side of the component;
 a C-shaped abutment-surrounding segment defining a concavity; and
 a connecting segment, such as an elongated connecting segment, joining the terminal screw attachment portion and the C-shaped abutment-surrounding segment. The component may optionally include further C-shaped abutment-surrounding segments and at least some adjacent C-shaped abutment-surrounding segments are connected by interposed connecting segments.

A related embodiment of the invention provides a one-piece, solid, such as metallic, elongated passively fitting framework component having a tissue side and an occlusal side, that includes or consists essentially of or consists of:
 a terminal screw attachment portion forming a hole passing from the tissue side to the occlusal side of the component;
 a first C-shaped abutment-surrounding segment;
 a first connecting segment, such as a first elongated connecting segment, joining the terminal screw attachment portion and the first C-shaped abutment-surrounding segment;
 a second C-shaped abutment-surrounding segment; and
 a second connecting segment, such as a second elongated connecting segment, joining the first C-shaped abutment-surrounding segment and the second C-shaped abutment-surrounding segment.

One embodiment of the invention provides a method for fabricating a passively fitting hybrid framework for a patient having at least two adjacent osseo-integrated dental implants in a jaw bone, there being two terminal dental implants, that includes the steps of:
 reversibly fixing an abutment sleeve to each dental implant other than a first one of the terminal dental implants;
 providing an elongated one-piece, optionally metallic, passively fitting framework component having a tissue side and an occlusal side, that includes:
  a terminal screw attachment portion forming a hole passing from the tissue side to the occlusal side of the component for attachment to an abutment of a terminal dental implant,
  a C-shaped abutment-surrounding segment defining a concavity for attachment to an abutment of each dental implant other than the first one of the terminal dental implants,
  a connecting segment, such as an elongated connecting segment, joining the terminal screw attachment portion and the C-shaped abutment-surrounding segment, wherein the elongated one-piece passively fitting framework component is sized and configured so that when the terminal screw attachment portion thereof is attached to the first one of the terminal dental implants in the patient's jawbone, the concavity of the C-shaped abutment-surrounding segment faces the secondary abutment sleeve;
 reversibly attaching the terminal screw attachment portion of the framework component to the first one of the terminal dental implants in the patient's mouth such that the C-shaped abutment-surrounding segment faces the abutment sleeve; and
 joining the C-shaped abutment-surrounding segment to the secondary abutment sleeve it faces with a hardening resin.

A related embodiment provides a method for fabricating a passively fitting hybrid framework in which the resin is used to joined components mounted on a model, that includes the steps of:
 providing a solid model of a patient's mouth with at least two osseo-integrated dental implants in a jaw bone there being two terminal dental implants;
 providing an elongated one-piece, optionally metallic, passively fitting framework component having a tissue side and an occlusal side that includes:
  a terminal screw attachment portion forming a hole passing from the tissue side to the occlusal side of the component for reversible attachment to a first terminal dental implant,
  a C-shaped abutment-surrounding segment defining a concavity for attachment to an abutment reversibly fixed to a dental implant other than the first terminal dental implant, and
  a connecting segment, such as an elongated connecting segment, joining the terminal screw attachment portion and the C-shaped abutment-surrounding segment;

reversibly attaching an abutment sleeve to a dental implant other than the first terminal dental implant in the model;

reversibly attaching the terminal screw attachment portion of the framework component to the first terminal dental implant of the model such that C-shaped abutment-surrounding segment at least partially surrounds the abutment sleeve; and joining the C-shaped abutment-surrounding segments to the at least partially surrounded abutment sleeve with a hardening resin.

In framework component embodiments including a screw attachment portion, there may be a single screw attachment portion, such as single terminal screw attachment portion, forming a hole passing from the tissue side to the occlusal side of the component of the embodiments. A screw attachment portion, such as a single screw attachment portion may also be located at a position to attach to a non-terminal dental implant where three or more dental implants are present.

The invention also provides embodiments in which, rather than an initial fixation of a framework component to an underlying dental implant via a screw attachment portion, such as a terminal screw attachment portion, of the framework component, the initial attachment of the framework component for setting the orientation for subsequent fixations is also made between an abutment sleeve (installed on a dental implant in the patient's mouth or on a model thereof), such as a secondary abutment sleeve, and a lateral face of the framework component that faces the sleeve, such as the face presented by a lateral concavity formed therein, such as the face of a lateral concavity presented by a C-shaped segment. The fabrication of a passively fitting framework according to such a method is exemplified in FIGS. 8-13.

Figure 8:
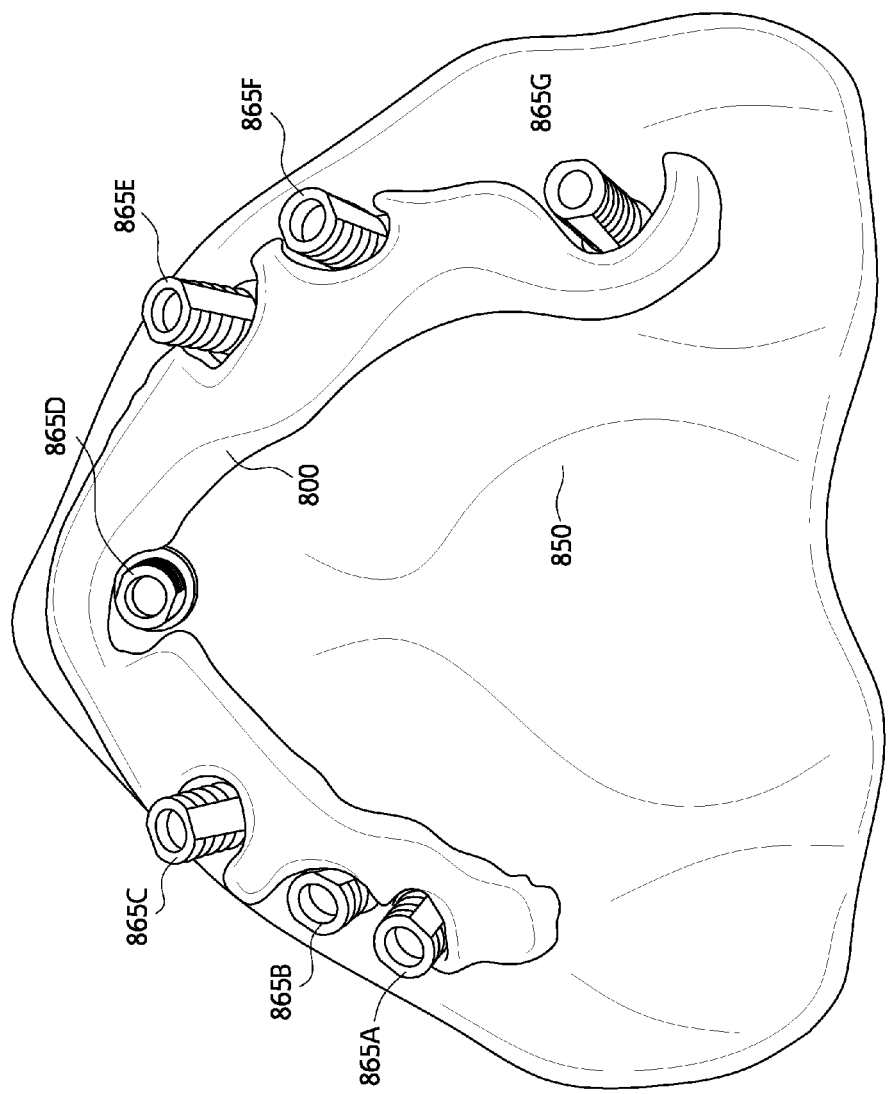
FIG. 8 shows a step in a resin-only method embodiment for fabricating a passively fitting framework.

FIG. 8 shows a hard model of a patient's mouth (maxillary), with seven dental implants installed in the maxilla. Secondary abutment sleeves 865A-865G, as shown, are already installed on the dental implants of the model. A unitary wax mock-up of a framework component 800 manufactured by conventional means (e.g., bending, cutting, filing) provides lateral concavities that face and at least partially surround the abutment sleeves. Generally, the mock-up of the framework component may be made from wax and/or acrylic, which can be burned out in a lost wax (investment) casting procedure to provide a corresponding metallic framework component. Rather than a casting process, a mock-up of a framework component may be three-dimensionally scanned and then three-dimensionally printed in a metallic or non-metallic material, such as by methods known in the art. If it is intended that the framework mock-up is to be scanned rather than cast, the framework mock-up may be made of any easily worked material (rather than only a material that can be burned out in a casting process). The shape and surface features of a metal framework component obtained by casting or other methods may, for example, be further refined if desired by machining or texturizing.

Figure 9:
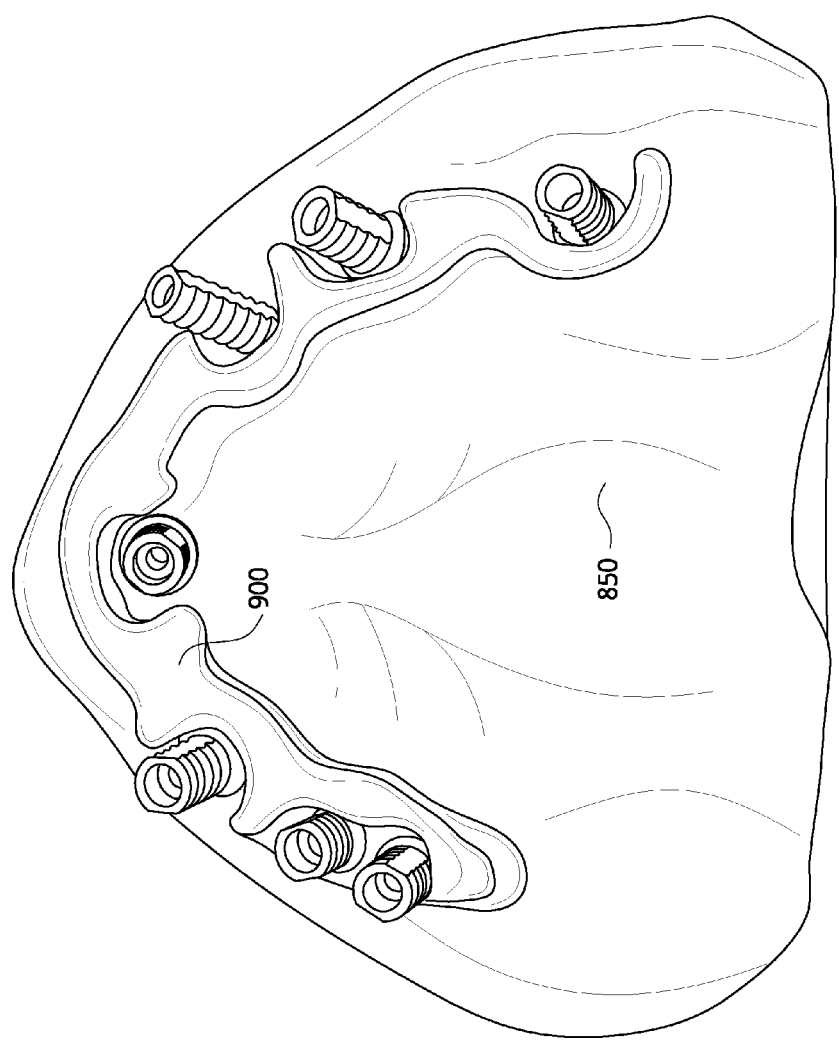
FIG. 9 shows a subsequent step in a resin-only method embodiment for fabricating a passively fitting framework.
Figure 10:
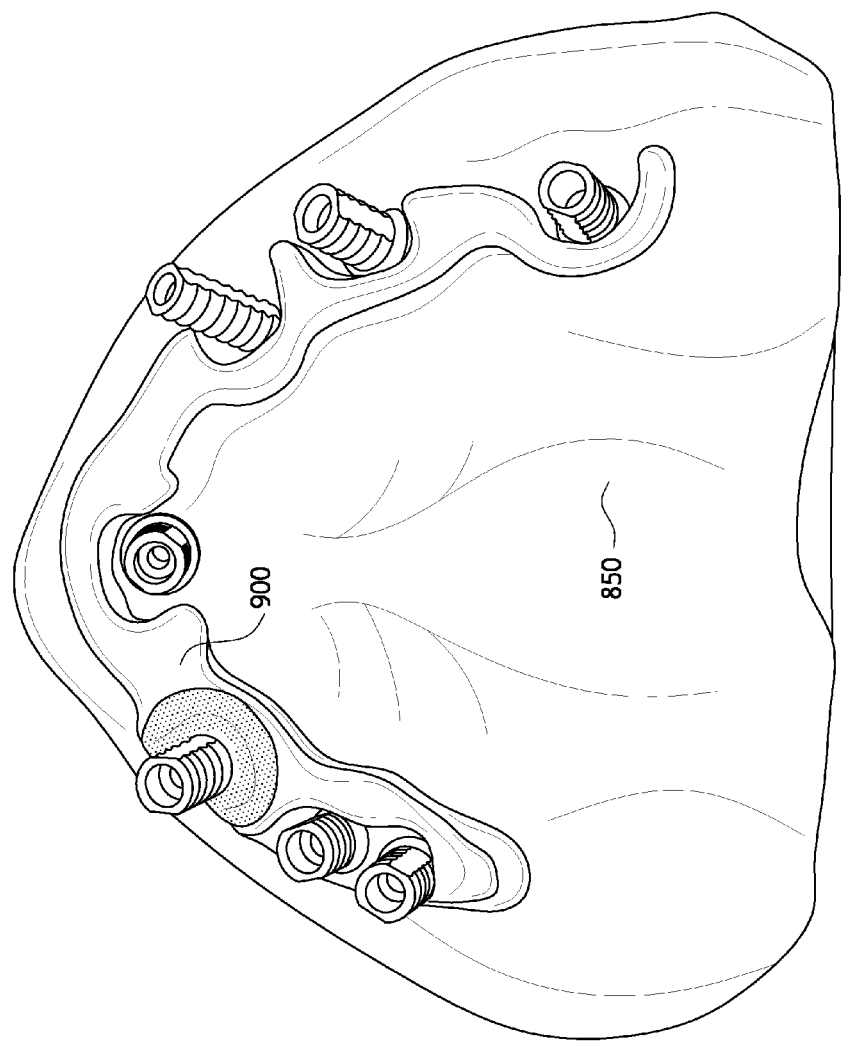
FIG. 10 shows a subsequent step in a resin-only method embodiment for fabricating a passively fitting framework.

FIG. 9 shows a metallic framework component 900, which was cast from framework mock-up 800, disposed on hard model 850 so that the abutment sleeves are laterally adjacent to and at least partially surrounded by the lateral concavities of framework 900. FIG. 10 shows resin 1000C filling the space between abutment sleeve 865C and framework 900 to join the abutment sleeve to the framework. Framework 900 joined to abutment sleeve 865C by hardened resin is then removed from the model as a unit by removing the internal screw securing abutment sleeve 865C to the underlying dental implant in the model.

Figure 11:
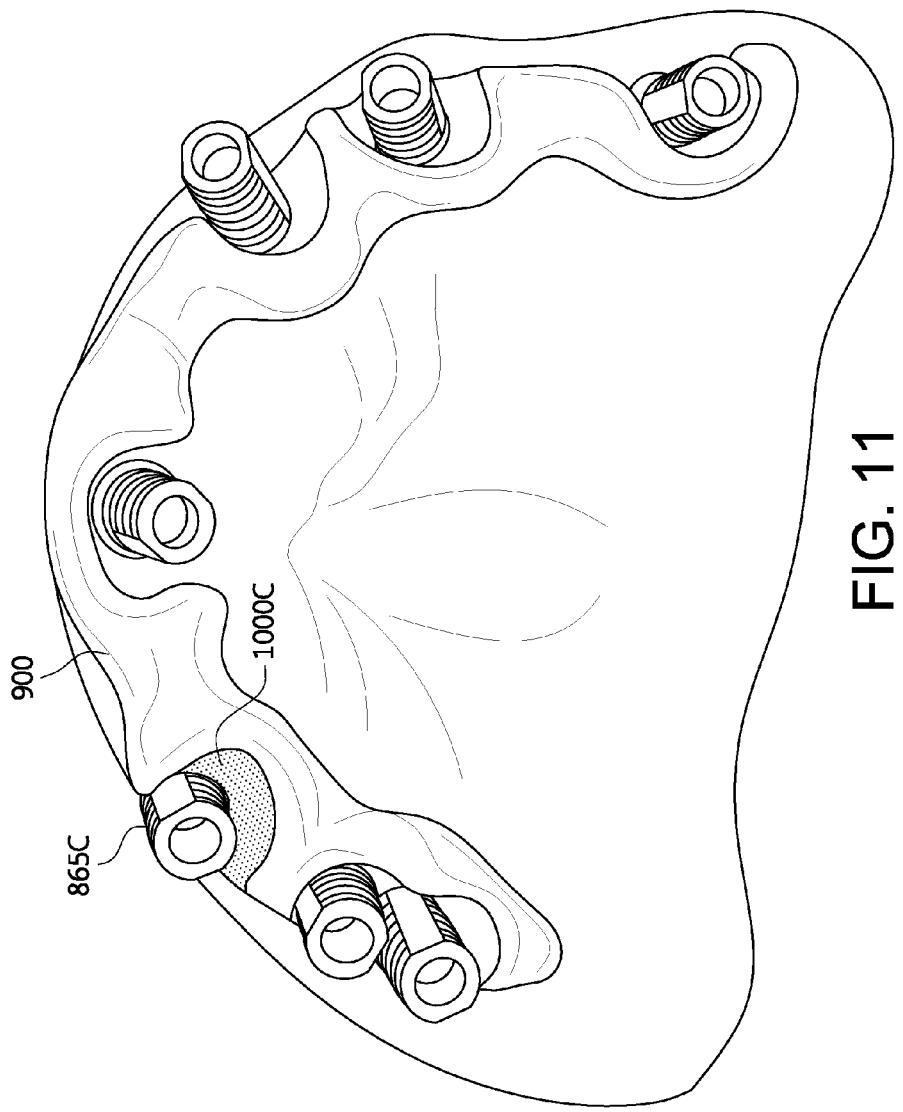
FIG. 11 shows a subsequent step in a resin-only method embodiment for fabricating a passively fitting framework.
Figure 12:
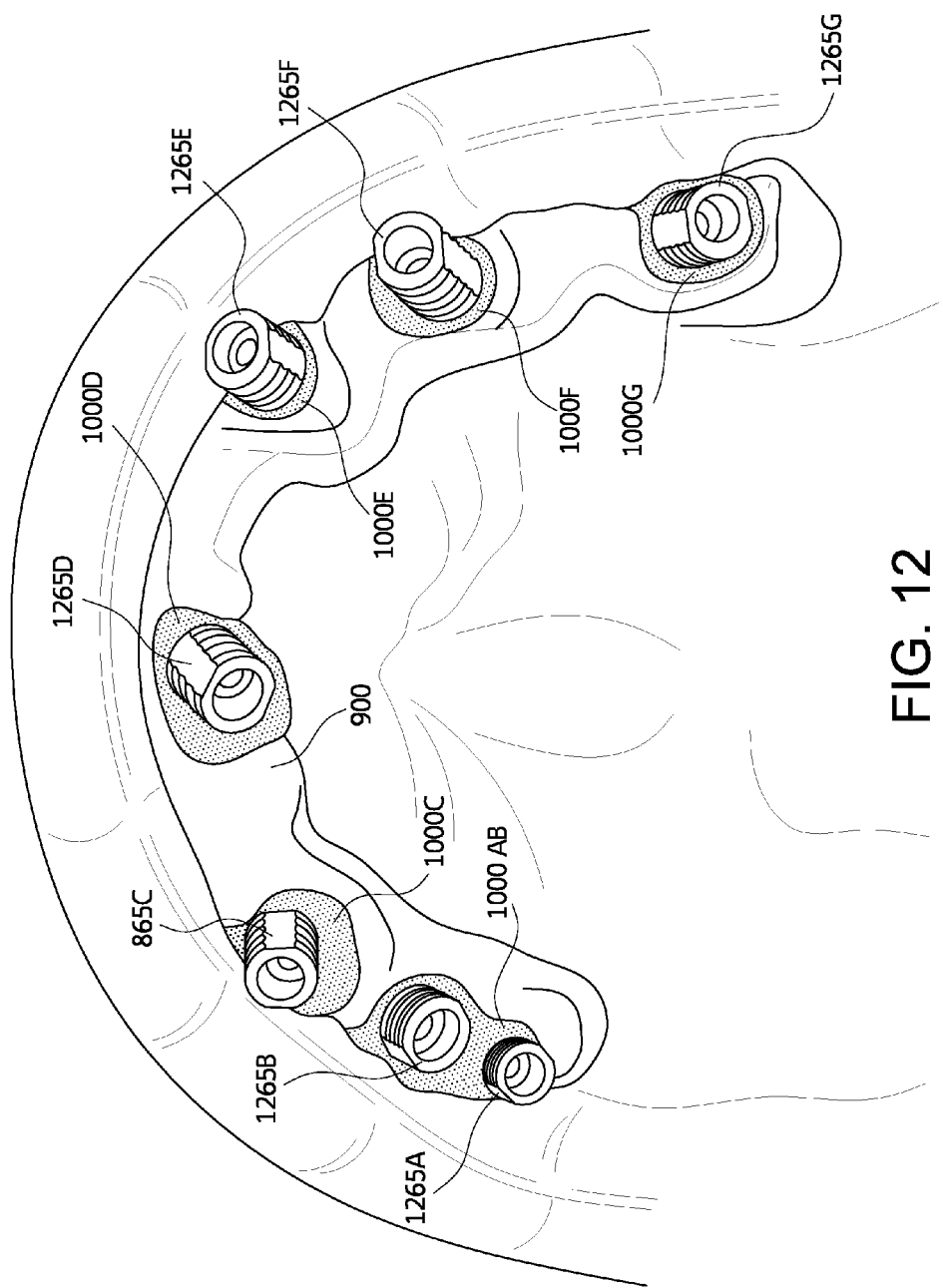
FIG. 12 shows a subsequent step in a resin-only method embodiment for fabricating a passively fitting framework.
Figure 13:
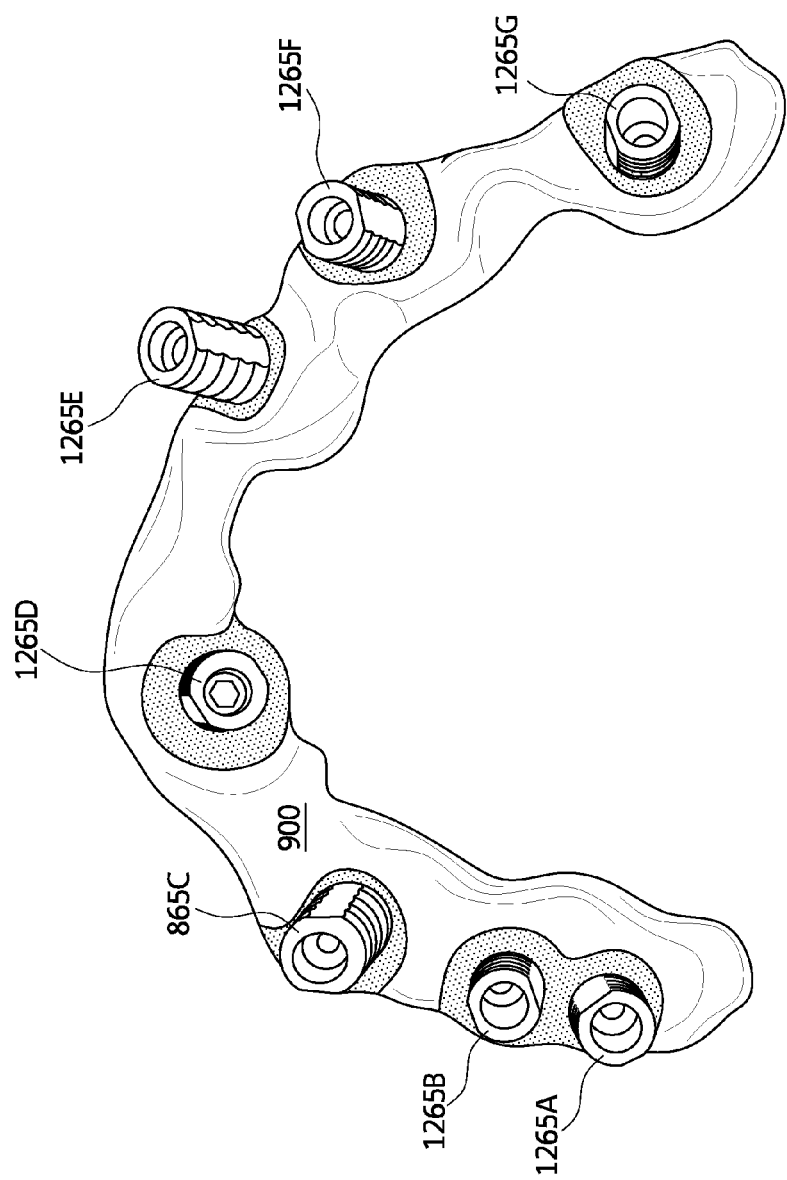
FIG. 13 shows the isolated, resin-only passively fitting framework obtained in the process shown in FIGS. 8-12.

FIG. 11 shows framework 900 resin-joined to abutment sleeve 865C now installed as a unit in the patient's mouth by screw attachment of abutment sleeve 865C to the corresponding dental implant in the patient's maxilla. Secondary abutment sleeves are shown already installed on the remaining dental implants in the patient's jaw. As shown, the remaining abutments are laterally juxtaposed to the lateral concave faces of framework 900. Each of the remaining abutments, 1265A-B and 1265D-G, is then joined with hardening resin to the adjacent portion of framework 900, with the result shown in FIG. 12 (resin shown at 1000A/B and 1000D-G, respectively). In this manner, a passively fitting prosthodontic framework is obtained. The resulting framework including framework component 900 and abutment sleeves 865C, 1265A-B and 1265D-G joined by resin to framework 900 is removed from the patient's mouth by unscrewing the screw member that secures each abutment sleeve to its respective dental implant. FIG. 13 shows the isolated passively fitting framework, which can then be further processed to provide a dental restoration including a tooth set-up.

Without limitation, the invention provides the following embodiments and variations thereof:

One embodiment of the invention provides a one-piece elongated passively fitting framework component having a tissue side and an occlusal side that includes or consists essentially of:

a first portion selected from the group consisting of a terminal screw attachment portion forming a hole passing from the tissue side to the occlusal side of the component and a terminal C-shaped abutment-surrounding segment defining a concavity;

a second portion which is a C-shaped abutment-surrounding segment defining a concavity; and a connecting segment, such as an elongated connecting segment, joining the first portion to the second portion. In one variation, there is a single screw attachment portion, such as a single terminal screw attachment portion, forming a hole passing from the tissue side to the occlusal side of the component. In another variation, there is no screw attachment portion forming a hole passing from the tissue side to the occlusal side of the component but there may be least two C-shaped segments. In a related variation, there is no terminal screw attachment portion forming a hole passing from the tissue side to the occlusal side of the component.

Another embodiment of the invention provides a one-piece, elongated passively fitting framework component having a tissue side and an occlusal side that includes or consists essentially of:

a first C-shaped abutment-surrounding segment;

a second C-shaped abutment-surrounding segment; and a connecting segment, such as an elongated connecting segment, joining the first C-shaped abutment-surrounding segment and the second C-shaped abutment-surrounding segment or the first and second C-shaped abutment-surrounding segments being directly joined.

A related embodiment of the invention provides a one-piece, elongated passively fitting framework component having a tissue side and an occlusal side that includes or consists essentially of:

a plurality of C-shaped abutment-surrounding segments sequentially ordered along the framework component; and for each pair of sequentially adjacent C-shaped abutment-surrounding segments, a connecting segment, such as an elongated connecting segment, joining sequentially adjacent C-shaped abutment-surrounding segments and/or sequentially adjacent C-shaped abutment-surrounding segments directly connected to each other or any combination thereof.

A further embodiment of the invention provides a method for fabricating a passively fitting framework for a patient having at least two adjacent osseo-integrated dental implants in a jaw bone, there being two terminal dental implants, that includes the steps of:

reversibly fixing an abutment sleeve to at least one of the dental implants;

providing an elongated one-piece, passively fitting framework component having a tissue side and an occlusal side that comprises:
 a first C-shaped abutment-surrounding segment,
 a second C-shaped abutment-surrounding segment, and
 a connecting segment, such as an elongated connecting segment, joining the first C-shaped abutment-surrounding segment and the second C-shaped abutment-surrounding segment or the first and second C-shaped abutment-surrounding segments being directly joined,
wherein the elongated one-piece passively fitting framework component is sized and configured so that if a secondary abutment sleeve is installed on each dental implant, the concavity of each of the C-shaped abutment-surrounding segments of the framework will face the secondary abutment sleeve of a dental implant;

positioning the framework in the patient's mouth so that the concavity of each C-shaped abutment-surrounding segment will face a secondary abutment sleeve installed on one of the dental implants; and joining at least one of the C-shaped abutment-surrounding segment to the secondary abutment sleeve it faces with a hardening resin.

Still another embodiment of the invention provides a method for fabricating a passively fitting framework that includes the steps of:

providing a solid model of a patient's jaw with at least two osseo-integrated dental implants in a jaw bone there being two terminal dental implants;

providing an elongated one-piece, passively fitting framework component having a tissue side and an occlusal side, that includes:
 a first C-shaped abutment-surrounding segment,
 a second C-shaped abutment-surrounding segment, and
 a connecting segment, such as an elongated connecting segment, joining the first C-shaped abutment-surrounding segment and the second C-shaped abutment-surrounding segment or the first and second C-shaped abutment-surrounding segments being directly joined,
wherein the elongated one-piece passively fitting framework component is sized and configured so that if a secondary abutment sleeve were installed on each dental implant in the model, each of the C-shaped abutment-surrounding segments of the framework would face the secondary abutment sleeve of a dental implant;

positioning the framework in the model so that if a secondary abutment sleeve were installed on each dental implant, each of the C-shaped abutment-surrounding segments of the frameworks would face the secondary abutment sleeve of a dental implant;

reversibly attaching a first abutment sleeve to a first dental implant in the model; and joining the C-shaped abutment-surrounding segment that at least partially surrounds the first abutment sleeve with a hardening resin.

The method embodiment may further include the steps of:

detaching as a unit from the model the framework component joined by resin to the first secondary abutment sleeve;

reversibly installing a secondary abutment sleeve on each implant in the patient's jawbone except for that corresponding to the first dental implant in the model;

reversibly installing the framework component joined by resin to the first secondary abutment sleeve by screw attachment of the first secondary abutment sleeve to the dental implant in the patient's jawbone that corresponds to the first dental implant in the model, such that concavities of the remaining C-shaped abutment-surrounding segments of the framework component respectively face the secondary abutment sleeves reversibly installed on the remaining dental implants; and joining each of said remaining C-shaped abutment-surrounding segments with a hardening resin to the secondary abutment sleeve that it faces.

The one-piece framework components may be sized and configured so that the lateral surface-presenting abutment-facing segments thereof, such as the aforementioned C-shaped segments, are disposed so that each (simultaneously) is laterally adjacent to and faces the vertical projection of a dental implant (in the model and mouth), which projections are actualized by the attachment of abutment sleeves to the implants. The concave faces of the C-shaped segments are preferably those that are laterally adjacent to and face, and may at least partially surround, the vertical projection of the dental implant. As shown, for example, by FIGS. 8-13 a single concavity-presenting abutment surrounding segment of a framework compound may face and at least partially surround more than one abutment sleeve at a time.

The concavity-presenting abutment surrounding segments, such as C-shaped abutment-surrounding segments, of any of the embodiments may include one or more protrusions extending radially inward from the bounding surface of the concavity.

The invention also provides hybrid passively fitting frameworks that include or consist essentially or consist of:
 an elongated passively fitting framework component according to any one of embodiments or variations thereof described herein;
 a secondary abutment sleeve disposed at least partially in and/or facing the concavity of each C-shaped abutment-surrounding segment; and
 a hardened resin joining each secondary abutment sleeve to the C-shaped abutment-surrounding segment defining the concavity in which the secondary abutment sleeve is at least partially disposed (and/or faces generally). At least some, such as at least one or all, of the secondary abutment sleeves may be externally ribbed. Non-ribbed secondary abutment sleeves may also be used. The secondary abutment sleeves may be metallic such as titanium or titanium alloy.

The invention further provides dental restorations for detachable, fixed attachment to osseo-integrated dental implants that include or consist essentially of or consist of: a hybrid passively fitting framework as and any variations thereof as described herein; and a tooth set-up attached to the hybrid passively fitting framework.

In any of the aforementioned method embodiments, the hardening resin may be a light-curable resin and the joining step may then further include illuminating the resin with a light source to cure the resin.

The methods of forming a hybrid framework may also optionally include a further step of: after joining the C-shaped abutment-surrounding segment to the at least partially surrounded secondary abutment sleeves with the hardening resin, welding at least one of the secondary abutment sleeves to the metallic framework component using a metallic spanning member. More particularly, the spanning member may be welded at one end to the secondary abutment sleeve and at the other end to the adjacent C-shaped abutment-surrounding segment.

In each of the method embodiments described, there may also be more than two dental implants, for example, 3, 4, 5, 6, 7, or 8, for which the framework is being prepared. In this case, as described herein, an abutment sleeve is reversibly attached to each of the dental implants, or to each one other than the first terminal dental implant, and an elongate framework component is provided that has a C-shaped abutment-surrounding member corresponding to each of the implant-attached abutment sleeves, the framework component being sized and configured so that when the screw attachment portion is reversibly attached to the first terminal dental implant, each of the C-shaped abutment-surrounding members at least partially surrounds (or faces, generally) the corresponding implant-attached abutment sleeve. Each of the C-shaped abutment-surrounding members can then be joined to the adjacent abutment sleeve using resin as described and, thereafter, optionally welded as described.

While the above embodiments and variations thereof have been exemplified with C-shaped concavity-presenting abutment-surrounding segments, which term is intended to be construed broadly with respect to shape and is inclusive of U-shaped and crescent-shaped, the invention also provides corresponding embodiments and variations thereof in which, more generally, lateral surface-presenting abutment-facing segments may be used such as, but not limited to, lateral concavity-presenting abutment-surrounding segments, such as but not limited to C-shaped and V-shaped abutment-surrounding segments. Any combination may be used according the invention. Furthermore, as shown throughout the figures, the segments of the framework component to which the abutments are joined using resin are not closed, i.e., are not closed rings which fully bound an aperture into which an abutment sleeve is disposed. Like the embodiments shown in the figures, the invention provides framework component embodiments in which none of the lateral surface-presenting abutment-facing segments present fully bounded apertures for surrounding an abutment sleeve. The invention also provides framework component embodiments in which at least one, at least two, at least two sequentially adjacent, at least three, at least some, or all of the lateral surface-presenting abutment-facing segments are laterally open (such as C-shaped or V-shaped) rather than closed in the manner of a fully bounded aperture sized to surround an abutment sleeve.

Each of the patent applications, patents and other publications cited in this disclosure is incorporated by reference as if fully set forth herein. Although the invention has been described in connection with specific preferred embodiments, it should be understood that the invention as claimed should not be unduly limited to these specific embodiments.

What is claimed is:

1. A hybrid passively fitting framework configured to support a tooth set-up on a plurality of dental implants, the framework consisting of:
   (i) a metallic elongated passively fitting framework component having a tissue side, an occlusal side, a labial side, a lingual side, and a length,
      wherein a first lateral concavity is formed in the labial side or the lingual side of the component, thereby providing a first concavity-presenting abutment-surrounding segment of the component which is laterally open,
      wherein a second lateral concavity is formed in the labial side or the lingual side of the component, thereby providing a second concavity-presenting abutment-surrounding segment of the component which is laterally open,
      wherein the first lateral concavity and the second lateral concavity are spaced apart along the length of the component, and
      wherein the component is one piece;
   (ii) a circumferentially continuous abutment disposed in and at least partially surrounded by each of the first and second lateral concavity-presenting abutment-surrounding segments, the circumferentially continuous abutment sleeve having a top, a bottom and a central shaft open at the top and the bottom, the circumferentially continuous abutment sleeve being spaced apart from the partially surrounding lateral concavity-presenting abutment-surrounding segment; and
   (iii) a hardened resin filled-in between each of the circumferentially continuous abutment sleeves and the partially surrounding lateral concavity-presenting abutment-surrounding segment, thereby joining said each circumferentially continuous abutment sleeve to the partially surrounding lateral concavity-presenting abutment-surrounding segment.

2. The hybrid passively fitting framework of claim 1, wherein at least one of the first and the second lateral concavity-presenting abutment-surrounding segments of the component is C-shaped.

3. The hybrid passively fitting framework of claim 1, wherein at least one of the circumferentially continuous abutment sleeves is externally ribbed.

4. A hybrid passively fitting framework configured to support a tooth set-up on a plurality of dental implants, the framework consisting of:
   (i) a metallic elongated passively fitting framework component having a tissue side, an occlusal side, a labial side, a lingual side and a length,
      wherein a plurality of lateral concavities are formed in one or both of the labial side and the lingual side of the component and spaced apart along the length of the component, thereby providing a plurality of lateral concavity-presenting abutment-surrounding segments of the component which are laterally open along the length of the component, and
      wherein the component is one piece;
   (ii) a circumferentially continuous abutment sleeve disposed in and at least partially surrounded by each of said plurality of lateral concavity-presenting abutment-surrounding segments, the circumferentially continuous abutment sleeve having a top, a bottom and a central shaft open at the top and the bottom, the circumferentially continuous abutment sleeve being spaced apart from the partially surrounding lateral concavity-presenting abutment-surrounding segment; and
   (iii) a hardened resin filled-in between each of the circumferentially continuous abutment sleeves and the partially surrounding lateral concavity-presenting abutment-surrounding segment, thereby joining each of the circumferentially continuous abutment sleeves to the partially surrounding lateral concavity-presenting abutment-surrounding segment.

5. The hybrid passively fitting framework of claim 4, wherein at least one of said plurality of lateral concavity-presenting abutment-surrounding segments has protrusions extending radially inward from the lateral concavity.

6. The hybrid passively fitting framework of claim 4, wherein at least one of the circumferentially continuous abutment sleeves is externally ribbed.

7. A dental restoration for removable attachment to osseointegrated dental implants, comprising:
   the hybrid passively fitting framework according to claim 4; and
   a tooth set-up attached to the hybrid passively fitting framework,
wherein the central shaft of each of the circumferentially continuous abutment sleeves is unobstructed by the tooth set-up.

8. The hybrid passively fitting framework of claim 1, wherein the first lateral concavity and the second lateral concavity are both formed in the labial side of the component or both formed in the lingual side of the component.

9. The hybrid passively fitting framework of claim 4, wherein all of the plurality of lateral concavities are formed in the labial side of the component or all of the plurality of lateral concavities are formed in the lingual side of the component.

10. An assemblage comprising:
    the hybrid passively fitting framework of claim 1;
    a dental implant for each of the circumferentially continuous abutment sleeves; and
    a retaining screw for each of the circumferentially continuous abutment sleeves, the retaining screw is configured to be inserted in the central shaft of each of the circumferentially continuous abutment sleeves to attach, the hybrid passively fitting framework to a dental implant.

11. An assemblage comprising:
    the hybrid passively fitting framework of claim 4;
    a dental implant for each of the circumferentially continuous abutment sleeves; and
    a retaining screw for each of the circumferentially continuous abutment sleeves, the retaining screw is configured to be inserted in the central shaft of each of the circumferentially continuous abutment sleeves to attach, the hybrid passively fitting framework to a dental implant.

12. The hybrid passively fitting framework of claim 1, wherein the framework is a fixed detachable framework.

13. The hybrid passively fitting framework of claim 4, wherein the framework is a fixed detachable framework.

14. The hybrid passively fitting framework of claim 1, wherein the circumferentially continuous abutment sleeves are metallic.

15. The hybrid passively fitting framework of claim 4, wherein the circumferentially continuous abutment sleeves are metallic.

* * * * *